United States Patent [19]

Sinkey

[11] 4,386,519
[45] Jun. 7, 1983

[54] SPECIFIC SURFACE FRACTIONATOR

[76] Inventor: John D. Sinkey, 686 White Oak Dr., Springfield, Ohio 45504

[21] Appl. No.: 114,211

[22] Filed: Jan. 22, 1980

[51] Int. Cl.³ .................... G01N 1/18; G01N 33/34
[52] U.S. Cl. .................................. 73/61.4; 209/211
[58] Field of Search .................. 73/61.4, 63, 432 PS; 209/211

[56] References Cited

U.S. PATENT DOCUMENTS 3,873,416  3/1975  Forgacs et al. ............... 73/63 X
4,135,389  1/1979  Karnis et al. .................. 73/61.4

Primary Examiner—E. R. Kazenske
Assistant Examiner—Joseph W. Roskos

[57] ABSTRACT

The specific surface distribution of a pulp may be obtained by pumping a sample at a pressure to overcome the pressure drop of a plurality of hydrocyclones arranged in series with the apex of leading hydrocyclones connected to the inlet of the next hydrocyclone, etc. in the series. Back pressure is maintained on the base outlet of the leading hydrocyclone, the consistency of the feed to the first hydrocyclone is sufficiently low to ensure that the consistency of the fraction rejected from the apex outlet of the penultimate hydrocyclone in the series is adequate for efficient separation in the final hydrocyclone of the series i.e. to have a feed consistency not exceeding about 0.25% to the last hydrocyclone in the series. Samples are collected from outlets from the hydrocyclones and may be tested to determine specific surface thereby to obtain an indication of the specific surface distribution of the pulp.

5 Claims, 2 Drawing Figures

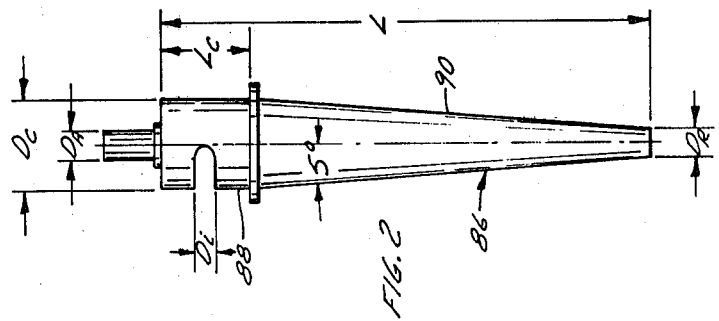
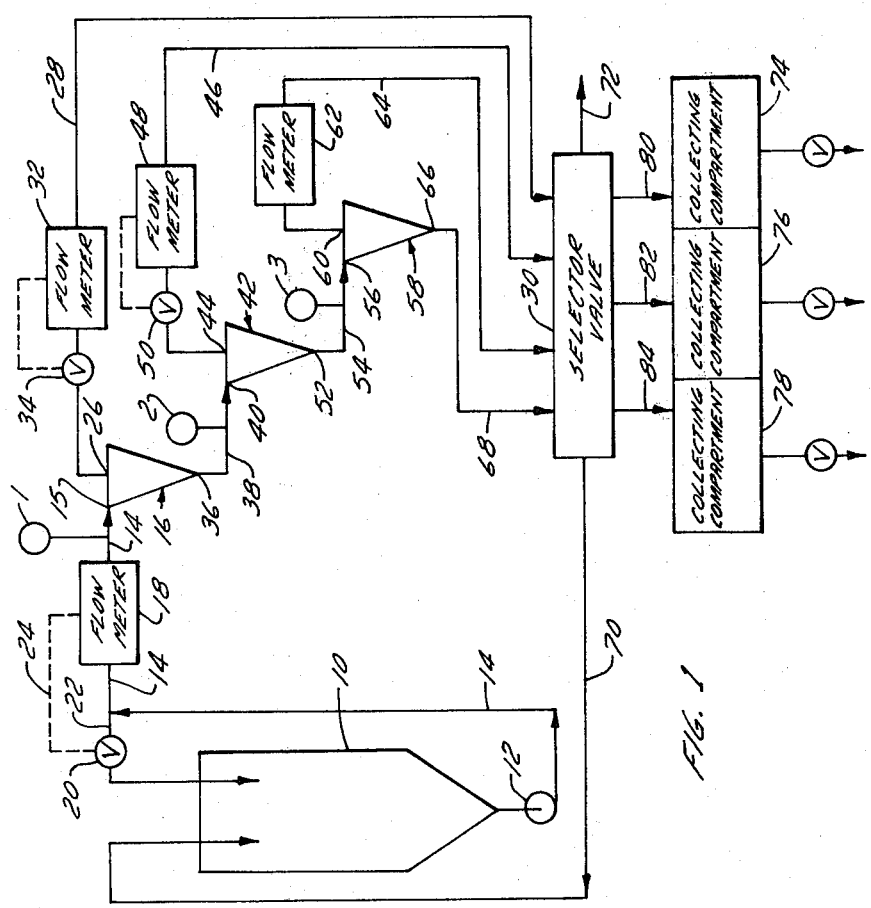

SPECIFIC SURFACE FRACTIONATOR

FIELD OF THE INVENTION

The present invention relates to a specific surface fractionator, more specifically the present invention relates to a simplified specific surface fractionator utilizing a special arrangement of hydrocyclones in series fed under high pressure using a very dilute slurry so that the total pressure drop across the cleaners is generated by a single pump and no dilution water need be added between cyclones.

BACKGROUND TO THE INVENTION

It has been proposed to examine the specific surface distribution of pulp using various techniques. For example, Canadian Pat. No. 1,045,866 issued Jan. 7, 1979 to Karnis and Wood described a technique utilizing a plurality of hydrocyclones arranged in series and measuring the various property of the accepts and rejects for these hydrocyclones. In this arrangement the accepts and/or rejects were individually collected and measured, the feed consistency adjusted and then pumped to the next hydrocyclones in the sequence to result in relative lengthy operation.

The fractionator described in the said Canadian patent was then superceded by a fractionator described in U.S. Pat. No. 4,135,389 issued Jan. 23, 1979 again to Karnis and Wood. This latter device is composed of a plurality of chambers with a hydrocyclone moveably mounted and connected to the various chambers so that the accepts or rejects as desired may be recycled through the hydrocyclone and various samples so produced analysed for specific surface. The procedure required to operate this device is time consuming in that it requires collecting a fraction, diluting the fraction to proper consistency and measuring the relevant properties and then feeding the diluted sample at the proper consistency through the hydrocyclone to provide another fraction and repeating the procedure.

BRIEF DESCRIPTION OF THE PRESENT INVENTION

The present invention overcomes some of these disadvantages of these prior art techniques by utilizing a feed pressure to the first cyclone sufficiently high to overcome the pressure drop through a plurality of hydrocyclones in series and by feeding the cellulose pulp to the first hydrocyclone at a consistency sufficiently low to insure that the feed consistency to the last hydrocyclone is less than about 0.25% and preferably no greater than 0.2%.

Broadly the present invention relates to a specific surface fractionator comprising; a plurality of hydrocyclones arranged in series, each of said cyclones having a conical section, a base outlet, an apex outlet and a tangential inlet; the apex outlet of each cyclone in said series being connected to the inlet of the next cyclone in said series, valve means connected to base outlets of said cyclones to maintain a back pressure on its respective base outlet to ensure the pressure at the apex outlet of its respective hydrocyclone is sufficiently high to overcome the pressure drop in the succeeding cyclones in said series and to obtain the desired flows to the other cyclones in said series, means for pumping a slurry to said inlet of the first cyclone in said series at a pressure sufficient high to overcome the pressure drop through said series of hydrocyclones, and means for collecting samples ejected from at least some of said outlets of said cyclones.

A method of separating a pulp on the basis of specific surface into a plurality of samples comprising; providing an arrangement of hydrocyclones in series, each of said hydrocyclones having a conical section, a base, a base outlet, an apex outlet and a tangential inlet adjacent said base; the apex outlet of each hydrocyclone connected to the inlet of the succeeding hydrocyclone in the arrangement, feeding a slurry of said pulp to a first hydrocyclone in said arrangement at a pressure sufficiently high to overcome the pressure drop through the arrangement and at a consistency to insure that the feed consistency to the last hydrocyclone in the arrangement is no greater than 0.25%, adjusting the flow through the base outlet of each of the cyclones in said arrangement to ensure that the pressure at the apex outlet of each of said cyclones is sufficiently high to overcome the pressure drop in the succeeding cyclones in said series and to obtain the desired rate of flow to the succeeding cyclones in said series, collecting fractions issuing from at least some of said outlets of said hydrocyclones.

BRIEF DESCRIPTION OF THE DRAWINGS

Further features, objects and advantages will be evident from the following detailed description of the preferred embodiments of the present invention taken in conjunction with the accompanying drawings, in which;

FIG. 1 is a schematic illustration of the present invention and

FIG. 2 is an illustration of a specific cyclone for use with the present invention.

DESCRIPTION OF THE PREFERRED EMBODIMENTS

Referring to FIG. 1, the present invention generally comprises, a sample tank 10, a pump 12, pumping the pulp sample from the tank 10 via a line 14 to the tangential inlet 15 of a first hydrocyclone 16. A flow meter 18 is provided in the line 14 and a bypass valve 20, in the return line 22 may be regulated by the flow meter 18 as indicated by the dash line 24 to obtain a certain flow rate into the hydrocyclone 16.

The base outlet 26 from the cyclone 16 is connected via a line 28 to a selector valve 30. A flow meter 32 is provided in the line 28 and operates a pressure valve 34 which adjusts the pressure at the base outlet 26 thereby controlling the pressure at the apex outlet 36 of cyclone 16 and the pressure in the line 38 which connects the apex outlet 36 directly with the tangential inlet 40 to next hydrocyclone 42.

The hydrocyclone 42 has a base outlet 44 which is connected by a line 46 to the selector valve 30. The flow through this line 46 is controlled by flow meter 48 which controls the valve 50 thereby to apply a back pressure at the base outlet 44 and maintain a pressure at the apex outlet 52 of the hydrocyclone 42 so that the pressure in line 54 connecting apex outlet 52 with the inlet 56 to hydrocyclone 58 is at a sufficiently high pressure to operate the third hydrocyclone 58. The flow from the base outlet 60 of hydrocyclone 58 is measured via flow meter 62 and is conducted by line 64 to a selector valve 30. The apex outlet 66 of hydrocyclone 58 is connected via line 68 to the selector valve 30.

Selector valve 30 is adapted to selectively connect the lines 28, 46, 64 and 68 to return line 70 to chamber 10, drain line 72 or lines 80, 82 or 84 to the collecting compartments 74, 76 and 78 respectively.

The pressure in lines 14, 38 and 54 feeding the cyclones 16, 42 and 58 respectively may be indicated by a suitable gauge indicated at 1, 2 and 3 respectively.

It will be apparent that the flow to the various cyclones diminishes; i.e. the flow to hydrocyclone 16 is obviously greater than the flow to hydrocyclone 42 which in turn is greater than the flow to hydrocyclone 58. For this reason the hydrocyclones should be of different sizes.

In the specific arrangement indicated suitable cyclones such as that indicated at 86 in FIG. 2 will preferably have cylindrical section 88 and a conical section 90 with a 5° cone angle and the various dimensions $D_i$=inlet diameter; $L_c$=the axial length of the cylindrical section 88; L=the total length of the hydrocyclone, $D_c$=the base diameter of the hydrocyclone; $D_a$=the base outlet diameter and $D_r$=the apex outlet diameter will be set according to the inlet flows to each hydrocyclone 16, 42 and 58.

A specific example of the present invention is defined by the dimensions of the various cyclones in inches in Table I.

TABLE I

| Cyclone | CYCLONE DIMENSIONS (in.) | | | | | |
|---|---|---|---|---|---|---|
| | $D_c$ | $D_i$ | $D_a$ | $D_r$ | L | $L_c$ |
| I | 4.50 | 0.75 | 0.75 | 0.50 | 49.75 | 4.50 |
| II | 3.00 | 0.516 | 0.625 | 0.375 | 31.56 | 2.00 |
| III | 2.00 | 0.375 | 0.433 | 0.125 | 23.00 | 2.00 |

With this specific arrangement, operating conditions preferably will be indicated in Table II.

TABLE II

| | OPERATING CONDITIONS | | | | | | |
|---|---|---|---|---|---|---|---|
| Stream | 18 | 26 | 38 | 44 | 54 | 60 | 68 |
| Psig | 91 | 59 | 56 | 23 | 20 | 0 | 0 |
| flow, l/min (gpm) | 138.4 (36.6) | 76.1 (20.1) | 62.3 (16.5) | 38.3 (10.1) | 24.0 (6.34) | 19.2 (5.1) | 4.8 (1.3) |
| fiber flow, O.D. g/min | 69.2 | — | 38 to 62 | — | 21 to 56 | — | 7 to 20 |
| % cons. | 0.05 | — | .06 to .10 | — | .08 to .23 | — | .14 to .42 |

In order to obtain a prescribed flow or the desired flows in any of the lines, flow meter readings at 18, 32 and 48 adjust the valves 20, 34 and 50 respectively to give the desired flow ratios. The flow meter 62 measures the flow in line 64.

With the arrangement described i.e. with the flow of 138 liters per minute line 14 leading into the first cyclone 16, the flow meter 32 and 48 control the base outlet flows so that rejects volume ratios (apex discharge) from cyclone 16 is approximately 45% of feed volume, from cyclone 42 approximately 38.5%. The reject rate from cyclone 58 is determined by the cyclone dimensions and is in the example approximately 25%.

It will be apparent that to operate the present invention, consistency in the tank 10 must be considerably less than the normal consistency used for pulp segregation in the cyclone since this consistency also governs the consistency in the feed to the cyclones 16, 42 and 58 and the consistency of the apex fractions is higher than the feed. If the consistency in the feed to any of the cyclones is too high (no greater than 0.25% and preferably 0.2%), the efficiency of the cyclone will be significantly affected. To meet this requirement the consistency in tank 10 should be sufficiently low to insure the consistency in line 56 is no greater than 0.25% and preferably about 0.2%. Simlarly the pressure in line 14 leading to the first cleaner 16 must be sufficiently high to ensure that the infeed pressure to the other cyclones is sufficiently high to obtain a reasonable cyclone operation i.e. high enough to overcome the pressure drop through the system.

In the operation of the device, the pulp sample in a tank 10 is pumped by pump 12 via line 14 to the inlet 15 of the first cyclone 16. The flow in this line is controlled by a flow meter 18 controlling by-pass valve 20 to by-pass certain percentage of the stock pumped by pump 12. Back pressure is maintained on the base outlet or accepts outlet 26 of this hydrocyclone 16 via the valve 34 which is controlled by flow meter 32, thereby to provide a pressure at the apex outlet 36 to feed the cyclone 42 and to set the % rejects (apex discharge) for the cyclone 16. A back pressure is maintained on the base outlet 44 of cyclone 42 via the valve 50 controlled by flow meter 48 thereby to provide a pressure at the apex outlet 52 sufficient to feed the third cleaner or hydrocyclone 58 and to control the amount of the rejects from the cyclone. Control of the reject rates also influences the consistency of the rejects which thus determines the consistency of the stock fed to the next cyclone in the series. The stock fed to cyclone 58 is divided into flows in the lines 64 and 68 with the flow in line 64 being measured by the flow meter 62.

Collection of the samples is controlled by the selector valve 30 as follows.

At start-up, all of the lines 28, 46, 64 and 68 are connected via line 70 to the tank 10 for re-circulation. This condition is maintained until stabilized operation of the hydrocyclones is obtained. After stabilization assuming the pulp in line 28 is of little interest, the selector valve connect line 28 to drain line 72 and the pulp from lines 46, 64 and 68 to tank 74, thereby to collect a sample of the pulp discharging from the apex of hydrocyclone 16 i.e. the pulp in line 38. When the required size of sample has been collected in tank 74 selector valve 30 is manipulated to direct line 46 together with line 28 to drain line 72 and to collect the pulp issuing from lines 64 and 68 in chamber 76. Again, when the required sample is accumulated in chamber 76, valve 30 is manipulated to direct the pulp from line 64 together with pulp from line 28 and 48 to drain line 72 and the pulp issuing from line 68 is accumulated in tank 78.

From the arrangement illustrated, three samples only are collected, however, if further samples are desired, it is a simple matter to revise the selector valve 30 to direct selected flows in to specific chambers. For example, if it were desired to obtain a sample from line 46 per se, a separate chamber could be provided to receive flow from this chamber rather than directing it to the drain.

Since the total flow to the system is measured by flow meter 18 and the flows in lines 28, 46, 64 are measured by the flow meters 32, 48, 62 the flow in line 68 can be calculated and therefore the qualities of the various samples taken is known. The samples may then be tested to obtain the specific surface of the various fractions collected and thereby obtain an indication of the specific surface distribution of the pulp.

Modifications may be made without departing from the spirit of the invention as defined in the appended claims.

I claim:

1. A specific surface fractionator comprising; a plurality of hydrocyclones arranged in series, each of said cyclones having conical section with a base, a base outlet, an apex outlet and a tangential inlet adjacent said base; means connecting the inlet of each cyclone to the apex outlet of the preceding cyclone, valve means regulating the flow through the base outlets of at least some of said cyclones to maintain a back pressure on their respective base outlet to ensure that the pressure at the apex outlet of their respective hydrocyclone is sufficiently high to overcome the pressure drop in the succeeding cyclones in said series and to obtain the desired flows to the succeeding cyclones in said series, means for pumping a slurry to said inlet of the first cyclone in said series at a pressure sufficient high to overcome the pressure drop in each of the hydrocyclones in the series, and means for collecting samples ejected from at least some of said outlets of said cyclones.

2. A specific surface fractionator as defined in claim 1 wherein said series of cyclones comprises; three of said cyclones in series.

3. A specific surface fractionator as defined in claims 1 or 2 further comprising; a flow meter measuring flow to said first hydrocyclone and controlling a valve in a bypass line thereby to regulate the flow to said first hydrocyclone, and a flow meter regulating each of said valve means to regulate the pressure at the apex outlet of each said cyclone of said series of cyclones.

4. A method of separating a pulp on the basis of specific surface into a plurality of samples comprising; providing an arrangement of hydrocyclones in series, each of said hydrocyclones having a conical section with a base, a base outlet, an apex outlet and a tangential inlet adjacent said base; the apex outlet of each hydrocyclone connected to the inlet of the succeeding hydrocyclone in the arrangement, feeding a slurry of said pulp to the inlet of a first hydrocyclone in said arrangement at a pressure sufficiently high to overcome the pressure drop through the arrangement and at a consistency to ensure that consistency of the feed to the last hydrocyclone in the arrangement is no greater than 0.25%, adjusting the flows through the base outlet of at least some of the cyclones in said arrangement to ensure that the pressure and flow at the apex outlet of each of said cyclones are sufficiently high to overcome the pressure drop in the succeeding cyclones in said series and provide pulp flow in the required amount and consistency for operation of the succeeding cyclones in said series, collecting fractions issuing from at least some of said outlets of said hydrocyclones.

5. A method as defined in claim 4 wherein the consistency of the feed to the last hydrocyclone in the arrangement in no greater than 0.2%.

* * * * *